(12) United States Patent
Houghton et al.

(10) Patent No.: US 7,375,106 B2
(45) Date of Patent: May 20, 2008

(54) SYNERGISTIC COMBINATION OF AN OPIOID ANALGESIC AND A NSAID

(75) Inventors: Andrea Houghton, Lanarkshire (GB); Jean Cottney, Lanarkshire (GB)

(73) Assignee: N.V. Organon (NL)

( * ) Notice: Subject to any disclaimer, the term of this patent is extended or adjusted under 35 U.S.C. 154(b) by 557 days.

(21) Appl. No.: 10/514,860

(22) PCT Filed: May 12, 2003

(86) PCT No.: PCT/EP03/50156

§ 371 (c)(1),
(2), (4) Date: Nov. 16, 2004

(87) PCT Pub. No.: WO03/097057

PCT Pub. Date: Nov. 27, 2003

(65) Prior Publication Data

US 2005/0153983 A1    Jul. 14, 2005

(30) Foreign Application Priority Data

May 16, 2002  (EP) .................................. 02076928

(51) Int. Cl.
*A61K 31/495* (2006.01)
(52) U.S. Cl. .................................. 514/255.04; 544/396
(58) Field of Classification Search ................ 544/396; 514/255.04
See application file for complete search history.

(56) References Cited

U.S. PATENT DOCUMENTS 5,516,803 A    5/1996  Raffa
5,681,830 A *  10/1997 Chang et al. ................. 514/85

FOREIGN PATENT DOCUMENTS

| EP | 0 711 289 | 7/1994 |
|---|---|---|
| EP | 0 649 657 A | 4/1995 |
| WO | WO 94 10987 | 5/1994 |

OTHER PUBLICATIONS

Picard, P. et al.: "Ketorolac potentiates morphine in postoperative patient-controlled analgesia" Pain (Aug. 1997) V73, p. 401-406, XP-002213157.

Cataldo et al., "Ketorolac and Patient Controlled Analgesia in the Treatment of Postoperative Pain," *Gynecol. Obstet. 176* (1993) 435-438.

Cordell et al., "Comparison of Intravenous Ketorolac, Meperidine, and Both (Balanced Analgesia) for Renal Colic," *Ann. Emerg. Med. 28* (1996) 151-158.

Ding et al., "Use of Ketorolac and Fentanyl During Outpatient Bynecologic Surgery," *Anesth. Analg. 77* (1993) 205-210.

Gupta et al., "Postoperative Pain Following Knee Arthroscopy: The Effects of Intra-articular Ketorolac and/or Morphine," *Reg. Anesth. Pain Med. 24* (1999) 225-230.

Joishy et al., "The Opioid-Sparing Effects of Intravenous Ketorolac as an Adjuvant Analgesic in Cancer Pain: Application in Bone Metastases and the Opioid Bowel Syndrome," *J. Pain Symptom Manag. 16* (1998) 334-339.

Popp et al., "A Comparison of Ketorolac Tromethamine/Oxycodone Versus Patient-Contolled Analgesia with Morphine in Anterior Cruciate Ligament Reconstruction Patients," *Arthroscopy 14* (1998) 816-819.

See et al., "An Outcome Study of Patient-Controlled Morphine Analgesia, With or Without Ketorolac, Following Radical Retropubic Prostatectomy," *J. Urol. 154* (1995) 1429-1432.

Sevarino et al., "The Efficacy of Intramuscular Ketorolac in Combination with Intravenous PCA Morphine for Postoperative Pain Relief," *J. Clin. Anesth. 4* (1992) 285-288.

Tallarida, et al., "Statistical analysis of drug-drug and site-site interactions with isobolograms," *Life Sci. 45* (1989) 947-961.

Tallarida "Statistical analysis of drug combinations for synergism," *Pain 49* (1992) 93-97.

Varassi et al., "A Double-Blinded Evaluation of Propacetamol Versus Ketorolac in Combination with Patient-Controlled Analgesia Morphine: Analgesic Efficacy and Tolerability After Gynecologic Surgery," *Anesth. Analg. 88* (1999) 611-616.

* cited by examiner

*Primary Examiner*—Zinna N. Davis
(74) *Attorney, Agent, or Firm*—Susan Hess

(57) ABSTRACT

The invention relates to a combined pharmaceutical preparation comprising an opioid diarylmethyl piperazine compounds and a NSAID. Such a preparation in which the compounds are either given sequentially or simultaneously can be used for the treatment of pain diminishing the side-effects observed in conventional opioid treatments.

2 Claims, 2 Drawing Sheets

Org 41793 with indomethacin

Figure 1:
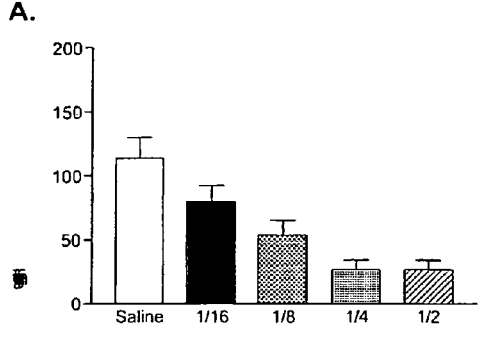
Figure 1:
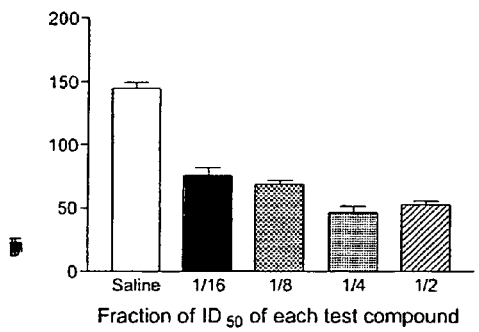
Figure 1:
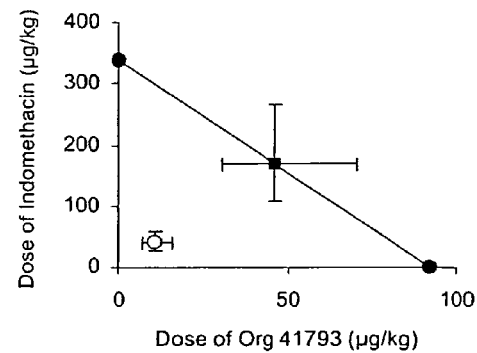
Figure 1:
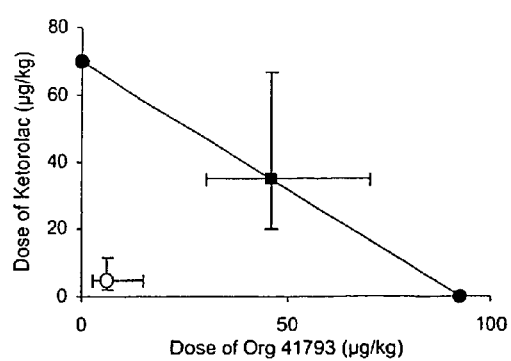

A.

C.

Org 41793 with ketorolac

B.

D.

Morphine with indomethacin

A.

B.

Morphine with ketorolac

C.

D.

SYNERGISTIC COMBINATION OF AN OPIOID ANALGESIC AND A NSAID

The invention relates to the field of analgesic combinations, more specifically combinations of opioid analgesics and non-steroidal anti-inflammatory drugs (NSAIDs). In particular this invention relates to the combination of opioid diarylmethyl piperazine compounds with a NSAID.

Opioid agonists have been used throughout the history of mankind to alleviate pain. The best known compounds in this group are morphine, codeine, pethidine, mepiridine, tramadol, sufentanil and fentanyl. These compounds are still heavily used in pain treatment, amongst others in the treatment of surgical, including post-operative, pain and to alleviate pain in terminally ill patients. Use of the opioid analgesics is, however, hampered by the side-effects of these drugs, which comprise respiratory depression, dependence (both physical and psychological), disorientation, profound sedation, muscle rigidity, urinary retention, nausea, vomiting and constipation. Opioid agonist drugs mediate their effects via an interaction with opioid receptors in the body. Three major types of opioid receptors have been identified: mu- (µ-), delta- (δ-), and kappa- (κ-) receptors. Morphine and its analogs have selectivity for the mu-opioid receptor, which appears to be involved in the generation of the above-mentioned side-effects.

Recently, a group of opioid diarylmethyl piperazine compounds has been disclosed (EP 0 711 289) which binds with high affinity to both the mu-, and delta-opioid receptors and which are especially useful in analgesia. Some of these compounds additionally bind to the kappa-opioid receptor. Preclinical evidence suggests that the side-effects of opioid drugs as discussed above are less severe with compounds which additionally bind to the delta-receptor.

Because of the severity of side-effects, combinations of opioid drugs with other analgesic drugs have been studied as a method to decrease the dose of the opioid drug. A group of analgesic drugs which has been considered in this respect are inhibitors of prostaglandin synthase, also called non-steroidal anti-inflammatory drugs (NSAIDs). Next to their anti-inflammatory actions these NSAIDs have analgesic action and are used in the treatment or prophylaxis of pain and inflammation, such as in rheumatoid arthritis, headache, neuralgia, dysmenorrhoea, dental pain and the like.

It has been reported in the scientific literature that a decrease in the dose of opioid analgesics is possible with concurrent administration of NS AIDs. Cataldo P. A., et al., (Surg. Gynecol. Obstet. 176: 435-438, 1993), Picard P., et al. (Pain 73: 401-406, 1997), See W. A, et al., (J. Urol. 154: 1429-1432, 1995) and several others report the effects of a combination of morphine and ketorolac tromethamine (Toradol) in post-operative pain relief. This combination also was found to be effective for pain treatment in cancer patients (Joishy S. K. and Walsh D., J. Pain Symptom Manag. 16: 334-339, 1998). Gupta A., et al. (Reg. Anesth. Pain Med. 24: 225-230, 1999) suggest that this same combination could be said to have a synergistic analgesic effect, while Sevarino F. B. et al. (J. Clin. Anesth. 4: 285-288, 1992) conclude that this combination has an additive effect.

Additional studies suggest that a combination of morphine and propacetamol has been found to be as effective in producing analgesia as a combination of morphine and ketorolac (Varassi G., et al., Anesth. Analg. 88: 611-616, 1999). In addition to concurrent administration of morphine with a NSAID, also combinations of ketorolac and oxycodone (Popp J. E., et al., Arthroscopy 14: 816-819, 1998), ketorolac and mepiridine (Cordell W. H., et al., Ann. Emerg. Med. 28: 151-158, 1996), and ketorolac and fentanyl (Ding Y., et al., Anesth. Analg. 77: 205-210, 1993) appeared to be effective.

A synergistic effect is reported with the combination of tramadol and ibuprofen (U.S. Pat. No. 5,516,803).

The prior art, however, does not disclose that a combination of a diarylmethyl piperazine opioid compound with another analgesic compound would be suitable for lessening the side-effects of each or to decrease the dosage of the opioid compound while still retaining sufficient analgesic effect.

We have demonstrated that a synergistic analgesic effect can be achieved by administration of a NSAID together with an opioid diarylmethyl piperazine according to the following general formula:

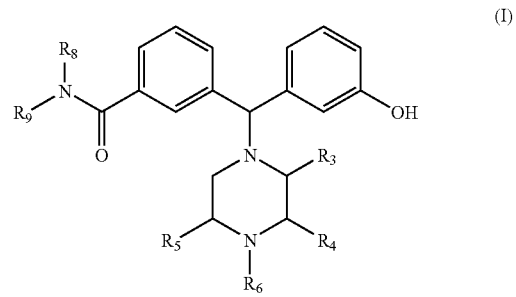

(I)

wherein:
$R^8$ is phenyl substituted with one or more constituents selected from halogen and trifluoromethyl, and $R^9$ is hydrogen, saturated $C_1$-$C_6$ hydrocarbyl or unsaturated $C_3$-$C_6$ hydrocarbyl;
one of $R^3$ and $R^5$ is methyl and the other and $R^4$ are both hydrogen or one is hydrogen and the other is methyl; and $R^6$ is hydrogen, saturated $C_1$-$C_6$ hydrocarbyl, unsaturated $C_3$-$C_6$ hydrocarbyl or $C_2$-$C_6$ methoxyalkyl;

or a pharmaceutically acceptable ether, ester or salt thereof or a physiologically functional derivative thereof.

As used herein, in reference to the present invention, the term "alkyl" is intended to be broadly construed as encompassing alkyl groups of straight chains as well as branched chain character.

As used herein, in reference to the present invention, the term "hydrocarbyl" is intended to encompass a group containing only carbon and hydrogen atoms which may contain triple bonds and which may be cyclic or aromatic in nature.

By "physiologically functional derivative" is meant a pharmaceutically acceptable salt, ester, ether or salt of an ester or an ether of the compound of formula (I) or any other compound which, upon administration to the recipient, is capable of providing (directly or indirectly) the said compound of formula (I) or an active metabolite or residue thereof. Phenolic $C_1$-$C_6$ alkyl ethers are a sub-class of physiologically functional derivatives of the compounds of formula (I).

A subclass of compounds within the scope of formula (I) are compounds wherein the hydrocarbyl group $R^6$ or $R^9$ is $C_1$-$C_6$ alkyl or $C_3$-$C_6$ cycloalkyl.

A subclass of compounds within the scope of formula (I) are compounds wherein $R^3$ and $R^5$ are both methyl and $R^4$ is hydrogen.

One preferred sub-class of compounds within the scope of the present invention comprises compounds wherein $R^6$ is unsaturated $C_3$-$C_6$ hydrocarbyl and preferably is allyl.

Most preferred is the compound 3-[(αR)-α-((2S,5R)-4-allyl-2,5-dimethyl-1-piperazinyl)-3-hydroxybenzyl]-N-(3-fluorophenyl)-N-methylbenzamide(=DPI-3290,   =Org 41793), which has the following formula:

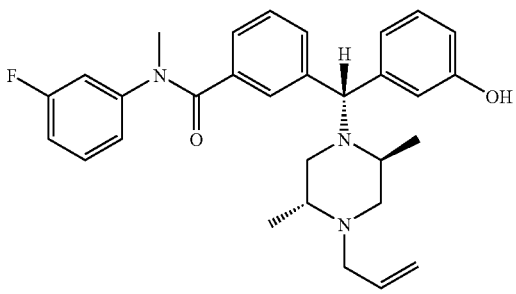

Equally preferred is the hydrochloride salt of Org 41793 (denominated Org 43273).

In the compositions and methods of treatment of the current invention the NSAID portion may be either a single NSAID, or a combination of one or more NSAIDs. Accordingly, as used herein, NSAID includes all of these possibilities. The ratio of the opioid drug according to formula (I) and the NSAID is from about 1:1 to 1:200, more preferably from about 1:2 to 1:20.

The NSAID and the opioid drug according to formula (I) can be administered subsequentially (in any order) or at the same time. It is also possible to administer both drugs in various administration forms, e.g. either or both may be administered by intravenous bolus or infusion, intramuscularly, orally, transdermally, rectally, sublingually, by aerosol, etc.

However, it is preferred to administer both drugs in one formulation. These combinations, comprising the opioid drug according to formula (I) and the NSAID, and when desired other pharmaceutical active compounds in an intimate mixture with a pharmaceutical carrier, can be prepared according to conventional pharmaceutical compounding techniques. The carrier may take a wide variety of forms depending on the form of preparation desired for administration, e.g. intravenous, oral or parenteral. The composition may also be administered by means of an aerosol. In preparing the combinations, in an oral dosage form, any of the usual pharmaceutical media may be employed. For example, in the case of oral liquid preparations (such as suspensions, elixirs and solutions), water, glycols, oils, alcohols, flavouring agents, preservative s, colouring agents an the like may be used. In the case of oral solid preparations (such as, for example, tablets, powders and capsules) carriers such as starches, sugars, diluents, granulating agents, lubricants, binders, disintegrating agents and the like may be used. Because of their ease of administration, tablets and capsules represent the most advantageous oral dosage forms. If desired, tablets may be sugar-coated or enteric-coated by standard techniques. For parenterals, the carrier will usually comprise sterile water, though other ingredients, for example to aid solubility or for preservative purposes or to make the solution isotonic, may be included. Injectable suspensions may also be prepared, in which case appropriate liquid carriers, suspending agents and the like may be employed. Examples of specific formulations useful in this invention can be found in EP 0 711 289.

NSAIDs according to the present invention are non-opioid analgesics characterised in that they are non-steroidal drugs which act as anti-inflammatory, analgesic and anti-pyretic agents. This class of drugs is well known in the art, see, for example, Chapter 26 of Goodman, L. and Gilman, A. ("The Pharmacological Basis of Therapeutics", 8th edition, Pergamon press, New York, 1990). Within this broad class of drugs are salicylates, such as aspirin; pyrazolone derivatives such as phenylbutazone, onyphenbutazone, antipyrine, aminopyrine, dipyrone, metamizol, phenazone, propyphenazone and apazone; indomethacin; sulindac; fenamates, such as mefenamic, meclofenamic, flufenamic, tolfenamic and etofenamic acids; COX-2 inhibitors such as 4-hydroxy-2-methyl-N-(5-methyl-2-thiazolyl)-2H-1,2-benzothiazine-3-carboxamide 1,1-dioxide (Meloxicam), 4-hydroxy-2-methyl-N-2-pyridyl-2H-1,2-benzothiazine-3-carboxamide-1,1-dioxide (Piroxicam), 4-[5-(4-methylphenyl)-3-(trifluoromethyl)-1H-pyrazol-1-yl]benzenesulfonamide (Celecoxib) and 4-[4-(methylsulfonyl)phenyl]-3-phenyl-2 (5H)-furanone (Rofecoxib), aryl acetic acid and propionic acid compounds such as 2-(p-isobutylphenyl)propionic acid (generic name ibuprofen), alphamethyl 4-(2-thienylcarbonyl) benzene acetic acid (generic name suprofen), 4,5-diphenyl-2-oxazole propionic acid (generic name oxprozin), rac-6-chloro-alphamethyl-carbazole-2-acetic acid (generic name carprofen), 2-(3-phenyloxyphenyl)-propionic acid, particularly the calcium salt dihydrate thereof (these compounds being referred to generically as fenoprofen an fenoprofen calcium); 2-(6-methoxy-2-naphtyl)propionic acid (generic name naproxen), 4-(1,3-dihydro-1-oxo-2H-isoindol-2-yl)-alpha-methylbenzene acetic acid (generic name indoprofen); 2-(3-benzoylphenyl)propionic acid (generic name ketoprofen); and 2-(2-fluoro-4-biphenylyl)propionic acid (generic name flurbiprofen) and 1-5-(4-methylbenzoyl)-1H-pyrrole-2-acetic acid (generic name tolmetin). Also included within NSAIDs are compounds within the class including sodium 5-(4-chlorobenzoyl)-1,4-dimethyl-1H-pyrrole-2-acetate dihydrate (generically referred to as zomepirac sodium); 4-hydroxy-2-methyl-N-2-pyridyl-2H-1,2-benzothiazine-3-carboxamide-1,1,-dioxide (generic name piroxicam), tenoxicam, 2',4'-difluoro-4-hydroxy-3-phenylcarboxylic acid (generic name diflunisal) or 1-isopropyl-7-methyl-4-phenyl-2 (1H)-quinozolinone (generic name proquazone), phenylacetic acid derivatives such as alclofenac, diclofenac, etodolac and (±)-5-benzoyl-2,3-dihydro-1H-pyrrolizine-1-carboxylic acid, 2-amino-2-(hydroxymethyl)-1,3-propanediol (generic name ketorolac tromethamine, toradol is a racemic mixture of [−]S and [+]R ketorolac tromethamine); and nabumetone. Especially preferred are ketorolac or indomethacin.

The method and compositions of the present invention are suitable for the treatment of pain. Any analgesic treatment is indicated, but the compositions of the invention are extremely useful in the treatment or prophylaxis of severe pain for which normally opioid drugs would be indicated, such as treatment of post-operative pain, pain in neoplastic patients, pain in terminal patients, anaesthesia, chronic pain (including back pain, neuropathic pain and arthritis), obstetric pain and dysmenorrhea.

However, since the dose of the opioid drug can be decreased with the co-administration of the NSAID, the treatment of pain with the combinations of the invention is also indicated in those cases which up till now would not be indicated for use of opioid drug therapy because of the side-effects of the opioids. Such cases are mild pain, acute pains, headache, spinal ache, gastralgia, and the like.

LEGENDS TO THE FIGURES

FIG. 1:

Graphs showing the effect on time spent licking in the period 20-30 min (Phase 2) following formalin injection, after combined administration of fractions of the $ID_{50}$ calculated in experiment 1 of A Org 41793 with indomethacin and C Org 41793 with ketorolac. On the right are isobolograms showing the interaction between B Org 41793 with indomethacin and D Org 41793 with ketorolac on the licking behaviour in Phase 2. The $ID_{50}$ values of each drug (O) are plotted on the X and Y axis. The line connecting both points is the theoretical line of additivity. The experimental $ID_{50}$ value of the fixed dose ratio (●) is found significantly below the respective additive point (■) in the isobologram; the confidence intervals do not overlap indicating a synergistic interaction. The 95% confidence intervals for the Org 41793 (horizontal) with ketorolac or indomethacin (vertical) components of the $ID_{50}$ are indicated for the experimental and additive $ID_{50}$ points. The theoretical additive $ID_{50}$ points and its 95% confidence intervals (CI) are calculated from the $ID_{50}$ values and CIs of each drug.

FIG. 2:

Graphs showing the effect on time spent licking in the period 20-30 min (phase 2) after formalin injection, after combined administration of fractions of the $ID_{50}$ calculated in experiment 1 of A morphine with indomethacin and C morphine with ketorolac. On the right are isobolograms showing the interaction between B morphine with indomethacin and D morphine with ketorolac in on the licking behaviour during Phase 2. The $ID_{50}$ values of each drug (O) are plotted on the X and Y axis. The line connecting both points is the theoretical line of additivity. The experimental $ID_{50}$ value of the fixed dose ratio (●) is found almost overlying the additive point (■) in the isobologram; the confidence intervals overlap indicating an additive interaction. The 95% confidence intervals for morphine (horizontal) with ketorolac or indomethacin (vertical) components of the $ID_{50}$ are indicated for the experimental and additive $ID_{50}$ points. The theoretical additive $ID_{50}$ points and its 95% confidence intervals (CI) are calculated from the $ID_{50}$ values and CIs of each drug.

EXPERIMENTAL PART

Methods

General

The formalin paw test is an animal model that assesses behavioural responses to continuous, noxious stimulation generated by injured tissue. The injection of a dilute solution of formalin into one hind paw of the mouse induces an inflammatory response in the paw, which is believed to provide a more valid model for clinical pain than acute tests using a phasic, high intensity stimulus (e.g. hot plate test). In mice, recording the time spent licking or biting the injected paw is the most common method of behavioural assessment. The test is sensitive for various classes of analgesic drugs e.g. opioids, cannabinoid agonists and non-steroidal anti-inflammatory drugs.

All experiments were carried out in accordance with the UK Animals (Scientific Procedures) Act 1986. Experiments were performed on male mice (Hsd Ola:ICR) from Harlan UK Ltd. (Bicester, UK). Subjects were grouped on receipt and acclimatised for a minimum of 5 days at a constant temperature (21°±1° C.) under a 12-hour light/12-hour dark cycle. Mice were tail-marked. At the end of the study all mice were euthanized with $CO_2$ or cervical dislocation.

Behavioural Testing Procedures

Procedures for Measuring Licking after Formalin Injection

Following subcutaneous formalin injection into the plantar surface of the paw, animals were placed in a Perspex box on a glass plate. A piece of black cardboard was placed on top of the box. A video camera (Sony) placed beneath the glass plate was then used to record the mice for 45 min after formalin injection. Six mice were observed simultaneously. The video camera was linked to a PC and the video images captured as MPEG files using a software package (Studio MP10). The MPEG file was later transferred to CD for offline analysis. A behavioural scoring program (The Observer) was then used to measure the time the mice spent licking the injected paw. Two blocks of time were analysed: 0-5 min (Phase 1) and 20-30 min (Phase 2). These two time periods were chosen to reflect the two phases of licking that typically occur after formalin injection.

Drugs

The hydrochloride salt of Org 41793 (Org 43273, batch B) is a solid powder (MW=524.08) supplied by Organon. Morphine sulphate pentahydrate, solid powder (MW=758.9) and indomethacin, solid powder (MW 357.81) were purchased from Sigma, UK. Ketorolac trometol (MW 376.4), a solution 10 mg/ml, was purchased from Roche Products Limited UK. Org 43273, the hydrochloride salt of Org 41793 will hereafter be referred to as Org 41793.

Org 41793 and morphine were dissolved in sterile physiological saline. Ketorolac was diluted in sterile physiological saline. Indomethacin was dissolved in 0.1% sodium carbonate in de-ionised water. Drug and vehicle preparations were made on the day of testing.

Method of Administration

All test agents were administered via a tail vein. For determination of $ID_{50}$ data (experiment 1 below), Org 41793, morphine, ketorolac or indomethacin were administered intravenously 15 minutes prior to subplantar injection of formalin. In experiments where the combination of agents was given (experiment 2 below) ketorolac, indomethacin or vehicle was administered intravenously immediately after intravenous injection of Org 41793, morphine or vehicle. Animals were weighed immediately prior to testing and all test agents were administered in a dosing volume of 5 ml/kg. Each animal was used once only.

Experiment 1

Determination of $ID_{50}$

Animals (n=6 for each dose/drug) received increasing doses of morphine, ketorolac, indomethacin, the hydrochloride salt of Org 41793 (Org 43273) or vehicle administered intravenously 15 min before injection of formalin (20 μl; 3%) into the plantar surface of the left hindpaw. Data were plotted as the mean time spent licking the formalin injected paw±s.e.m for each of the two time periods (0-5 & 20-30 min) and an $ID_{50}$ for the group calculated. To calculate the $ID_{50}$ for the second phase of licking, the time spent licking following test drug treatment was calculated as a percentage of the time spent licking by vehicle-treated mice. An $ID_{50}$ was then calculated using a non-linear regression fit, sigmoidal dose-response with constants of 0 and 100 for the bottom and top, respectively (GraphPad Prism software).

All of the test compounds (Org 41793, morphine, ketorolac and indomethacin) resulted in a dose-dependent inhibition of Phase 2 licking. An $ID_{50}$ was calculated for the Phase 2 licking (i.e. 20-30 min after formalin injection; see Table 1), for each compound. The calculated $ID_{50}$ values for Org 41793, morphine, indomethacin and ketorolac were 92, 870, 340 and 70 µg/kg, respectively. These values were used in experiment two.

Table 1 shows the calculated $ID_{50}$ values and 95% confidence intervals for the second phase of licking in the formalin paw test for each of the four test compounds.

TABLE 1

| Compound | $ID_{50}$ (µg/kg) for $2^{nd}$ phase of licking (95% confidence limits) |
|---|---|
| Org 41793 | 92 (60-140) |
| Morphine | 870 (496-1522) |
| Indomethacin | 340 (218-531) |
| Ketorolac | 70 (40-134) |

Experiment 2

Investigation of the Interaction Using Isobolographic Analysis

The $ID_{50}$ values calculated in experiment 1 for the second phase licking as previously described were used for this experiment. A dose-response curve was then obtained after co-administration of either Org 41793 or morphine with indomethacin or ketorolac in a constant dose ratio based on the $ID_{50}$ values of the single agents (treatments with ½, ¼, ⅛ and ¹⁄₁₆ of the $ID_{50}$ value of every drug, n=6per dose/drug combination). The $ID_{50}$ of the total dose of the mixture was then calculated from this dose-response curve.

To obtain a value for describing the magnitude of the interaction between Org 41793 with ketorolac or indomethacin, a total dose fraction value was then calculated using the following formula:

$$\frac{ID_{50} \text{ dose of drug 1 in combination}}{ID_{50} \text{ of drug 1 alone}} + \frac{ID_{50} \text{ dose of drug 2 in combination}}{ID_{50} \text{ of drug 2 alone}}$$

where drug 1 is Org 41793 or morphine and drug 2 is ketorolac or indomethacin. Values near 1 indicate additive interaction, values greater than 1 imply an antagonistic interaction, and values less than 1 indicate a synergistic interaction. Testing for a significant difference by t-test was not possible since confidence intervals (CIs) were not symmetric around the theoretical additive $ID_{50}$. Therefore, $ID_{50}$ values were considered to be significantly different (P<0.05) from each other, if the 95% confide nce intervals s of these points did not overlap (Tallarida R. J., Pain, 49, 93-97, 1992 and Tallarida et al. *Statistical analysis of drug-drug and site-site interactions with isobolograms.* Life Sci., 45, 947-961, 1989).

All of the four combinations (Org 41793+ketorolac; Org 41793+indomethacin; morphine+ketorolac; morphine+indomethacin) resulted in a dose-dependent inhibition of Phase 2 licking. The $ID_{50}$ for each combination is shown in Table 2.

The isobolographic analysis of Org 41793 and indomethac in revealed a synergistic interaction between the two compounds (FIG. 1). The theoretical $ID_{50}$ for an additive interaction was 46 µg/kg (30-70 µg/kg) of Org 41793 and 170 µg/kg (109-264.5 µg/kg) of indomethacin. However, the experimental $ID_{50}$ of Org 41793 and indomethacin was 11 µg/kg (7-16 µg/kg) and 40 µg/kg (26-58 µg/kg), respectively; the confidence intervals do not overlap indicating a synergistic interaction. The total dose fractional value was 0.23, also indicating a synergistic interaction (see Table 2).

Similarly, the isobolographic analysis of Org 41793 with ketorolac revealed a synergistic interaction between the two compounds (FIG. 1). The theoretical $ID_{50}$ for an additive interaction was 46 µg/kg (30-70 µg/kg) of Org 41793 and 35 µg/kg (20-67 µg/kg) of ketorolac. However, the experimental $ID_{50}$ of Org 41793 with ketorolac was 6 µg/kg (3-16 µg/kg) and 5 µg/kg (2-12 µg/kg), respectively; the confidence intervals do not overlap indicating a synergistic interaction. The total dose fractional value was 0.12, also indicating a synergistic interaction (see Table 2).

Figure 2:
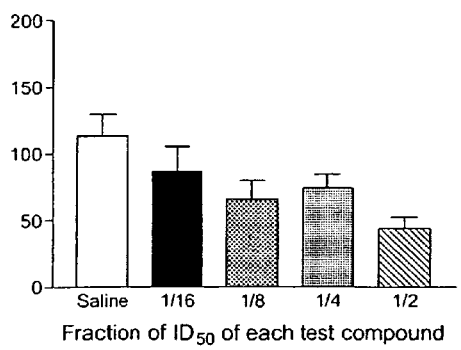
Figure 2:
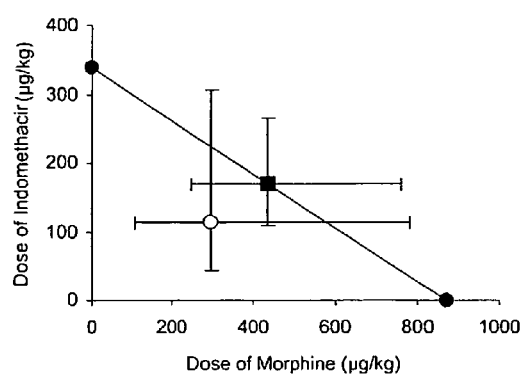
Figure 2:
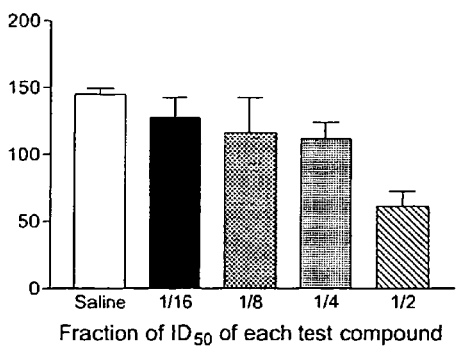
Figure 2:
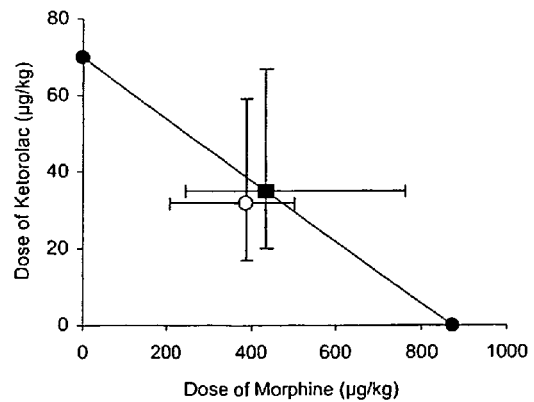

In contrast, the isobolographic analysis of morphine with indomethacin (FIG. 2) revealed only an additive interaction between the two compounds. The theoretical $ID_{50}$ for an additive interaction was 435 µg/kg (248-761 µg/kg) of morphine and 170 µg/kg (109-265 µg/kg) of indomethacin. However, the experimental $ID_{50}$ of morphine with indomethacin was 293 µg/kg (107-783 µg/kg) and 115 µg/kg (42-306 µg/kg), respectively; the confidence intervals overlap indicating an additive interaction. The total dose fractional value was 0.67, a value relatively close to 1, also indicating an additive interaction (see Table 2).

Similarly, the isobolographic analysis of morphine with ketorolac (FIG. 2) revealed an additive interaction between the two compounds. The theoretical ID 5 for an additive interaction was 435 µg/kg (248-761 µg/kg) of morphine and 35 µg/kg (20-67 µg/kg) of ketorolac. The experimental $ID_{50}$ of morphine with ketorolac was 391 µg/kg (209-504 µg/kg) and 32 µg/kg (17-59 µg/kg), respectively; the confidence intervals overlap indicating an additive interaction. The total dose fractional value was 0.91, also indicating an additive interaction (see Table 2).

The data from this study indicate that both ketorolac and indomethacin are opioid sparing, reducing the amount of morphine or Org 41793 required to elicit antinociception in the second phase of licking in the formalin paw test. A difference between the two opioids is that the interaction between Org 41793 with ketorolac or indomethacin was synergistic whereas the interaction between morphine with ketorolac or indomethacin was additive.

Table 2 shows the theoretical $ID_{50}$ values and experimental $ID_{50}$ values and 95% confidence intervals for the second phase of licking in the formalin paw test for each of the four combinations of drug administration Org 41793 with ketorolac, Org 41793 with indomethacin, morphine with ketorolac and morphine with indomethacin. The table also shows the total dose fraction, values near 1 indicate additive interaction, values greater than 1 imply an antagonistic interaction, and values less than 1 indicate a synergistic interaction.

TABLE 2

| Compounds | Theoretical ID$_{50}$ (μg/kg) for 2$^{nd}$ phase of licking (95% confidence limits) | Experimental ID$_{50}$ (μg/kg) for 2$^{nd}$ phase of licking (95% confidence limits) | Total Dose Fraction |
|---|---|---|---|
| Org 41793 with ketorolac | Org 41793: 46 (30-70) Ketorolac: 35 (20-67) | Org 41793: 6 (3-16) Ketorolac: 5 (2-12) | 0.12 |
| Org 41793 with indomethacin | Org 41793: 46 (30-70) Indomethacin: 170 (109-264) | Org 41793: 11 (7-16) Indomethacin: 40 (26-58) | 0.23 |
| Morphine with ketorolac | Morphine: 435 (248-761) Ketorolac: 35 (20-67) | Morphine: 391 (209-504) Ketorolac: 32 (17-59) | 0.91 |
| Morphine with indomethacin | Morphine: 435 (248-761) Indomethacin: 170 (109-264) | Morphine: 293 (107-783) Indomethacin: 115 (42-306) | 0.67 |

The invention claimed is:

1. A method for the treatment of pain in a patient in need thereof, comprising:

administering to the patient an effective amount of a non-steroidal anti-inflammatory drug (NSAID) and a diarylmethyl piperazine oploid analgesic according to formula (I):

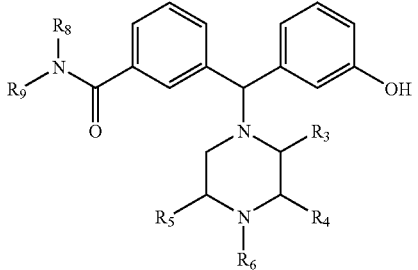

wherein:

R$^8$ is phenyl substituted with one or more constituents selected from halogen and trifluoromethyl, and R$^9$ is hydrogen, saturated C$_1$-C$_6$ hydrocarbyl or unsaturated C$_3$-C$_6$ hydrocarbyl;

R$^3$ and R$^5$ are each independently hydrogen or methyl, at least one of them being methyl;

R$^4$ is hydrogen or methyl, except that when R$^3$ and R$^5$ are both methyl R$^4$ is hydrogen; and R$^6$ is hydrogen, saturated C$_1$-C$_6$ hydrocarbyl, unsaturated C$_3$-C$_6$ hydrocarbyl or C$_2$-C$_6$ methoxyalkyl;

or a pharmaceutically acceptable ether, ester or salt thereof or a physiologically functional derivative thereof.

2. The method according to claim 1, wherein the opioid compound and the NSAID are administered simultaneously.

* * * * *

UNITED STATES PATENT AND TRADEMARK OFFICE
CERTIFICATE OF CORRECTION

PATENT NO.          : 7,375,106 B2                                    Page 1 of 1
APPLICATION NO. : 10/514860
DATED                 : May 20, 2008
INVENTOR(S)        : Andrea Houghton and Jean Cottney It is certified that error appears in the above-identified patent and that said Letters Patent is hereby corrected as shown below:

In the Claims:

Claim 1, col. 9, line 23, Please correct "oploid" to:

-- opioid --

Signed and Sealed this

Fifteenth Day of June, 2010

David J. Kappos
*Director of the United States Patent and Trademark Office*